(12) United States Patent
Smith et al.

(10) Patent No.: US 11,413,402 B2
(45) Date of Patent: Aug. 16, 2022

(54) SAFETY NEEDLE DEVICE

(71) Applicant: Becton, Dickinson and Company, Franklin Lakes, NJ (US)

(72) Inventors: Peter Smith, Cary, NC (US); Laurie Sanders, Glen Ridge, NJ (US); Edward P. Browka, Sherrill, NY (US); Paul P. Marici, Piscataway, NJ (US); Eli B. Nichols, Durham, NC (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 374 days.

(21) Appl. No.: 16/849,674

(22) Filed: Apr. 15, 2020

(65) Prior Publication Data

US 2020/0238020 A1  Jul. 30, 2020

Related U.S. Application Data

(62) Division of application No. 15/837,011, filed on Dec. 11, 2017, now Pat. No. 10,661,026.

(Continued)

(51) Int. Cl.
*A61M 5/32* (2006.01)
*A61M 5/158* (2006.01)
*A61M 25/06* (2006.01)

(52) U.S. Cl.
CPC .......... *A61M 5/3245* (2013.01); *A61M 5/158* (2013.01); *A61M 5/3243* (2013.01);
(Continued)

(58) Field of Classification Search
CPC ............. A61M 5/3257; A61M 5/3243; A61M 5/3202; A61M 5/3269; A61M 25/0637; A61M 25/0618; A61M 2005/325
See application file for complete search history.

(56) References Cited

U.S. PATENT DOCUMENTS

| 4,610,667 A | 9/1986 | Pedicano et al. |
| 4,795,432 A | 1/1989 | Karczmer |

(Continued)

FOREIGN PATENT DOCUMENTS

| CA | 2551835 A1 | 8/2005 |
| CA | 2803761 A1 | 12/2011 |

(Continued)

OTHER PUBLICATIONS

Non-Final Office Action in U.S. Appl. No. 15/837,748 dated Oct. 17, 2019, 19 pages.

(Continued)

*Primary Examiner* — Tiffany Legette
(74) *Attorney, Agent, or Firm* — Servilla Whitney LLC

(57) ABSTRACT

A safety needle device is disclosed having a housing configured to couple to a syringe, the housing having a proximal end, a distal end, and a housing body. A needle hub is disposed on the proximal end of the housing and a needle cannula is attached to the needle hub. The device having a retractable sheath configured to move between an initial position, a retracted position and an extended position with respect to the housing, wherein the initial position partially exposes a distal tip of the needle cannula, the retracted position fully exposes the needle cannula, and the extended position fully covers the distal tip of the needle cannula. The safety needle device may include an activation latch, a lockout latch, a tether and a spring element to bias the retractable sheath to an extended state to cover the distal end of the needle cannula upon completion of an injection. The safety needle device may include a slider element disposed above an activation latch. A method of drug delivery is also disclosed.

10 Claims, 14 Drawing Sheets

Related U.S. Application Data

(60) Provisional application No. 62/433,350, filed on Dec. 13, 2016.

(52) U.S. Cl.
CPC ........ *A61M 5/3269* (2013.01); *A61M 5/3273* (2013.01); *A61M 25/0618* (2013.01); *A61M 25/0625* (2013.01); *A61M 25/0631* (2013.01); A61M 5/3202 (2013.01); A61M 5/3257 (2013.01); A61M 5/3275 (2013.01); A61M 2005/325 (2013.01); A61M 2005/3246 (2013.01); A61M 2005/3258 (2013.01)

(56) References Cited

U.S. PATENT DOCUMENTS

| | | |
|---|---|---|
| 4,813,940 A | 3/1989 | Parry |
| 4,950,250 A | 8/1990 | Haber et al. |
| 5,084,028 A | 1/1992 | Kennedy et al. |
| 5,330,899 A | 7/1994 | Devaughn |
| 5,336,199 A | 8/1994 | Castillo et al. |
| 5,395,347 A | 3/1995 | Blecher et al. |
| 5,415,645 A | 5/1995 | Friend et al. |
| 5,591,138 A | 1/1997 | Vaillancourt |
| 5,688,241 A | 11/1997 | Asbaghi |
| 5,984,899 A | 11/1999 | D'Alessio et al. |
| RE36,885 E | 9/2000 | Blecher et al. |
| 6,884,237 B2 | 4/2005 | Asbaghi |
| 6,926,697 B2 | 8/2005 | Malenchek |
| 7,134,550 B2 | 11/2006 | Groth |
| 7,320,682 B2 | 1/2008 | Cocker et al. |
| 7,361,159 B2 | 4/2008 | Fiser et al. |
| 7,513,888 B2 | 4/2009 | Sircom et al. |
| 7,665,605 B2 | 2/2010 | Erickson et al. |
| 7,811,261 B2 | 10/2010 | Rubinstein et al. |
| 7,871,397 B2 | 1/2011 | Schraga |
| 8,048,036 B2 | 11/2011 | Woehr et al. |
| 8,062,265 B2 | 11/2011 | Millerd |
| 8,162,882 B2 | 4/2012 | Rubinstein et al. |
| 8,303,541 B2 | 11/2012 | Chun |
| 8,333,738 B2 | 12/2012 | Millerd |
| 8,439,870 B2 | 5/2013 | Moyer et al. |
| 8,496,627 B2 | 7/2013 | Chelak et al. |
| 8,636,688 B2 | 1/2014 | Shaw |
| 8,636,703 B2 | 1/2014 | Foshee et al. |
| 8,647,307 B2 | 2/2014 | Gratwohl et al. |
| 8,663,129 B2 | 3/2014 | Allen et al. |
| 8,747,355 B2 | 6/2014 | Rubinstein et al. |
| 8,827,961 B2 | 9/2014 | Emmott et al. |
| 8,968,241 B2 | 3/2015 | Liversidge |
| 8,979,794 B2 | 3/2015 | Chevallier |
| 9,050,416 B2 | 6/2015 | Feret et al. |
| 9,061,106 B2 | 6/2015 | Roberts et al. |
| 9,067,024 B2 | 6/2015 | Roberts et al. |
| 9,186,466 B2 | 11/2015 | Zachek et al. |
| 9,352,099 B2 | 5/2016 | Roberts et al. |
| 9,352,100 B2 | 5/2016 | Ward et al. |
| 9,352,101 B2 | 5/2016 | Roberts et al. |
| 9,370,327 B2 | 6/2016 | Teoh |
| 9,408,632 B2 | 8/2016 | Erskine |
| 9,445,760 B2 | 9/2016 | Allen et al. |
| 9,694,140 B2 | 7/2017 | Rubinstein et al. |
| 9,848,810 B2 | 12/2017 | Allen et al. |
| 2001/0031949 A1 | 10/2001 | Asbaghi |
| 2002/0063074 A1 | 5/2002 | Simm et al. |
| 2002/0165497 A1 | 11/2002 | Greene |
| 2003/0093009 A1 | 5/2003 | Newby et al. |
| 2003/0120209 A1 | 6/2003 | Jensen et al. |
| 2003/0121815 A1 | 7/2003 | Bergeron et al. |
| 2003/0181867 A1 | 9/2003 | Bressler et al. |
| 2004/0102740 A1 | 5/2004 | Meloul |
| 2005/0067309 A1 | 3/2005 | Choi |
| 2005/0113750 A1 | 5/2005 | Targell |
| 2005/0119627 A1* | 6/2005 | Crawford ............ A61M 5/3243 604/110 |
| 2005/0279664 A1 | 12/2005 | Hommann |
| 2006/0189933 A1 | 8/2006 | Alheidt et al. |
| 2006/0213793 A1 | 9/2006 | Brand |
| 2009/0024093 A1 | 1/2009 | Carrel et al. |
| 2009/0254042 A1 | 10/2009 | Gratwohl et al. |
| 2009/0299295 A1 | 12/2009 | Rubinstein et al. |
| 2010/0298770 A1 | 11/2010 | Rubinstein et al. |
| 2011/0276007 A1 | 11/2011 | Denenburg |
| 2011/0288491 A1 | 11/2011 | Newman et al. |
| 2012/0029440 A1 | 2/2012 | Boyd et al. |
| 2014/0048433 A1 | 2/2014 | Dasbach et al. |
| 2014/0097111 A1 | 4/2014 | Dasbach et al. |
| 2014/0135706 A1 | 5/2014 | Rubinstein et al. |
| 2014/0228772 A1 | 8/2014 | Ward et al. |
| 2014/0364803 A1 | 12/2014 | Rubinstein et al. |
| 2015/0034516 A1 | 2/2015 | Chapin et al. |
| 2015/0182704 A1 | 7/2015 | Chevallier |
| 2015/0190580 A1 | 7/2015 | Imai et al. |
| 2015/0297837 A1 | 10/2015 | Schraga |
| 2016/0074572 A1 | 3/2016 | Spool et al. |
| 2016/0303331 A1 | 10/2016 | Evans et al. |
| 2017/0106136 A1 | 4/2017 | Dibiasi |
| 2017/0233168 A1 | 8/2017 | Horvath et al. |
| 2018/0161490 A1 | 6/2018 | Sanders et al. |
| 2018/0161492 A1 | 6/2018 | Sanders et al. |
| 2018/0161521 A1 | 6/2018 | Sanders et al. |

FOREIGN PATENT DOCUMENTS

| | | |
|---|---|---|
| CN | 103079610 A | 5/2013 |
| EP | 0409180 A1 | 1/1991 |
| EP | 0734739 A2 | 10/1996 |
| EP | 0750915 A2 | 1/1997 |
| EP | 1537890 A1 | 6/2005 |
| EP | 1949928 A1 | 7/2008 |
| EP | 2585146 B1 | 3/2017 |
| FR | 2884723 A1 | 10/2006 |
| JP | H03139363 A | 6/1991 |
| JP | 2007519474 A | 7/2007 |
| JP | 2010502316 A | 1/2010 |
| JP | 2013523197 A | 6/2013 |
| JP | 2013529973 A | 7/2013 |
| MX | 2013/000081 A | 3/2013 |
| MX | 349289 B | 7/2017 |
| WO | 03/045480 A1 | 6/2003 |
| WO | 2008028305 A1 | 3/2008 |
| WO | 2009040602 A1 | 4/2009 |
| WO | 2009/114777 A1 | 9/2009 |
| WO | 2012/000833 A1 | 1/2012 |
| WO | 2012/013587 A1 | 2/2012 |

OTHER PUBLICATIONS

Non-Final Office Action in U.S. Appl. No. 15/837,756 dated Oct. 17, 2019, 39 pages.
Non-Final Office Action in U.S. Appl. No. 15/837,810 dated Oct. 17, 2019, 27 pages.
PCT International Search Report and Written Opinion in PCT/US2017/065689, dated Jan. 2, 2019, 18 pgs.
PCT International Search Report and Written Opinion in PCT/US2017/065716 dated Mar. 21, 2018, 14 pages.
PCT International Search Report and Written Opinion in PCT/US2017/065717 dated Mar. 19, 2018, 12 pages.
PCT International Search Report and Written Opinion in PCT/US2017/065718 dated Jan. 2, 2019, 18 pages.
PCT invitation to Pay Additional Fees and, Where Applicable, Protest Fee in PCT/US2017/065689 dated Feb. 20, 2018, 12 pages.
PCT Invitation to Pay Additional Fees, and, Where Applicable, Protest Fee in PCT/US2017/065718 dated Apr. 9, 2018, 13 pages.

* cited by examiner

SAFETY NEEDLE DEVICE

CROSS-REFERENCE TO RELATED APPLICATIONS

This application is a divisional of U.S. patent application Ser. No. 15/837,011, filed on Dec. 11, 2017, which claims priority under 35 U.S.C. § 119(e) to U.S. Provisional Application No. 62/433,350, filed Dec. 13, 2016, the disclosures of which are incorporated herein by reference in their entirety.

TECHNICAL FIELD

The present disclosure relates generally to a safety needle device, and specific embodiments pertain to a single-use passive safety needle device having a housing, a needle hub, a needle cannula, a retractable sheath, an activation latch, a lockout latch, a tether and a spring to bias the retractable sheath in a distal direction to cover the distal end of the needle cannula.

BACKGROUND

Needle devices are used throughout the medical industry for the injection and withdrawal of a wide variety of fluids and solutions into and from the human body. Because of the numerous potential hazards associated with the handling and manipulation of bodily fluids, and particularly blood, there are a number of known safety features that are frequently incorporated into various types of needle devices to protect the practitioner from accidental exposure to the needle.

Prior safety needle devices include several disadvantages including having a retractable sheath requiring long stroke distances to activate the safety feature, multi-component retraction and locking elements, and conveying an undesirable significant force against a patient's skin during activation of the safety feature upon receiving an injection. Conventional retraction syringe assemblies often also do not incorporate reuse prevention features, and thus, the retraction mechanism of the syringe may be reset so the syringe barrel may be reused. The reuse of syringe assemblies without sterilization or sufficient sterilization is believed to facilitate the transfer of contagious diseases. Further, the retraction features of conventional syringes may also require the practitioner to actively activate the retraction mechanism. Accordingly, the chance of human error in failure to activate or properly activate the retraction mechanism can lead to continued exposure of needles leading to needle stick injuries.

Some known retracting sheath safety needle devices have been developed to include a single-use safety needle device assembly that obscures a substantial majority or an entirety of an injection needle from view before, during, and after an injection procedure. However, many injection procedures require that the practitioner know precisely the location and depth to which the needle is inserted in the patient's tissue to be sure that medication is delivered to an appropriate location. In addition, there exists a tendency for many practitioners to falsely assume that they were "safe" from needle stick injuries, even in the non-locked initial state, due to the tip of the prior art retracting sheath safety needle devices being fully covered in an unlocked state.

Thus, there is a need in the art to provide a safety needle device having a passive activation mechanism that overcomes the deficiencies of the known retracting sheath safety needle devices and which allows for shorter stroke distance, ease of use, low part count, low part complexity, relatively compact design, and clear and unobstructed view of needle in an initial position.

SUMMARY

One aspect of the present disclosure pertains to a safety needle device including a housing configured to couple to a syringe. The housing includes a proximal end, a distal end, and a housing body. A needle hub may be disposed on the proximal end of the housing and a needle cannula may be attached to the needle hub. An activation latch may be disposed on an outer surface of the housing body and a retractable sheath may be disposed on an inner surface of the housing body. The retractable sheath may include a proximal end and a distal end. A retention shelf may be disposed on the proximal end of the retractable sheath. A lockout latch may be disposed on the retractable sheath to cover a distal tip of the needle cannula. The retention shelf is releasably engaged to the activation latch in an initial position, wherein the initial position partially exposes the distal tip of the needle cannula. A spring element is disposed in the housing body and attached to the distal end of the retractable sheath. In one or more embodiments, the safety needle device is a single use device. In one or more embodiments, the safety needle device is a passively activated device in which the safety features provide post-injection needle shielding without additional intervention by the user.

In one or more embodiments, the safety needle device may include a tether. In one or more embodiments, the tether may be a telescoping tether. In one or more embodiments, the telescoping tether includes a first end attached to the housing body and a second end attached to the retractable sheath. In yet another embodiment, the telescoping tether includes a plurality of substantially concentric shells. The tether may extend to form an enclosure around the cannula as retractable sheath is moved distally along the length of the cannula.

In one or more embodiments, movement of the retractable sheath from the initial position to a retracted position disengages the activation latch of the housing from the retention shelf on the proximal end of the retractable sheath.

In one or more embodiments, the lockout latch may be a metal latch.

In one or more embodiments, movement of the retractable sheath from the retracted position to an extended position engages the lockout latch to a distal tip of the needle cannula. The engagement of the lockout latch to the distal tip of the needle cannula inhibits reuse of the device by inhibiting translation of the retractable sheath. The spring element biases the retractable sheath toward the extended position.

In one or more embodiments, the retractable sheath translates from the initial position to the retracted position upon an active depression of the activation latch.

In one or more embodiments, the needle cannula is obscured from view when the retractable sheath is in the extended position.

In one or more embodiments, the spring element may be a coil spring.

Another aspect of the present disclosure pertains to a safety needle device, including a housing configured to couple to a syringe, the housing having a proximal end, a distal end, and a housing body. A needle hub may be disposed on the proximal end of the housing and a needle cannula may be attached to the needle hub. An activation latch may be disposed on an outer surface of the housing body and a slider element may be positioned in a longitudinal slot disposed over the activation latch. The longitudinal slot may include a forward slot end and a rear slot end. A retractable sheath may be disposed on an inner surface of the housing body, the retractable sheath having a proximal end and a distal end. A retention shelf may be disposed on the proximal end of the retractable sheath. A lockout latch may be disposed on retractable sheath to cover a distal tip of the needle cannula. The retention shelf releasably may be engaged to the activation latch in an initial position, wherein the initial position partially exposes the distal tip of the needle cannula; and a spring element disposed in the housing body and attached to the distal end of the retractable sheath.

In one or more embodiments, the slider element includes a contact surface having a profile for accommodating a practitioner's finger.

In one or more embodiments, the slider element may be in an initial protective position in which the slider element is at the forward slot end of longitudinal slot and extends over the distal end of the activation latch.

In one or more embodiments, the slider element may be in a non-protective position in which the slider element is at the rear end slot and extends over the proximal end of the activation latch allowing the activation latch to release from the retention shelf of the retractable sheath.

Another aspect of the present disclosure pertains to a method of drug delivery including obtaining the safety needle device described herein in a safe state in which a distal tip of a needle cannula is covered; requiring a practitioner to makes a first choice whether to a) fill the safety needle device with a desired liquid solution or b) Inject a patient; requiring a practitioner to makes a second choice based on the first choice to fill the safety device; and requiring a practitioner to makes a third choice based on the second choice.

In one or more embodiments, the second choice may be whether to: a) fill the safety needle device again, b) move the product to an inject state, or c) move the product to a transport state.

In one or more embodiments, after moving the product to the transport state, the safety device needle is moved to into a safe state. In one or more embodiments, the safe state includes placing a cap on the safety device needle.

Another aspect of the present disclosure pertains to a method of drug delivery including obtaining the safety needle device described herein in a safe state having a needle covered with a cap and a slider element positioned to prevent an activation latch from disengaging from a retention shelf of a retractable sheath; requiring a practitioner to makes a first choice whether to (a) fill the safety needle device by removing the cap and sliding the slider element over the activation latch to prevent activation latch from disengaging from the retention shelf of the retractable sheath while filling the device or (b) inject by removing the cap and insert the needle into a patient to deliver medication; requiring a practitioner to makes a second choice based on the first choice to fill the safety device; and requiring a practitioner to makes a third choice based on the second choice.

In one or more embodiments, the second choice may be whether to: a) fill the safety device needle repeatedly over a desired number of times, b) move the product to an inject state by sliding the slider mechanism off of the activation latch to allow for the release of the activation latch from the retention shelf on the retractable sheath during inject state to allow for retractable sheath with its protective clip to cover the distal tip of the needle cannula, or c) move the product to a transport state by re-capping the safety needle device with a cap.

In one or more embodiments, the third choice may be whether to actively change the state of product by removing the cap and moving the slider element to allow release of the activation latch from the retention shelf on the retractable sheath to the inject state.

DETAILED DESCRIPTION

Figure 1:
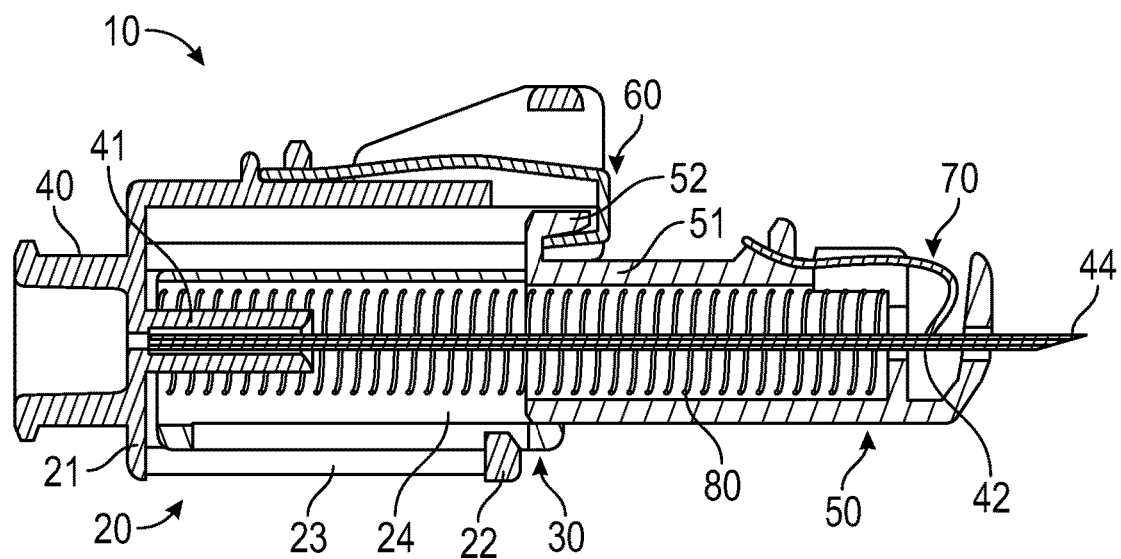
FIG. 1 illustrates an exploded view of a safety needle device according to a first embodiment.

Before describing several exemplary embodiments of the present disclosure, it is to be understood that the embodiments of the present disclosure are not limited to the details of construction or process steps set forth in the following description. The embodiments of the present disclosure are capable of other embodiments and of being practiced or being carried out in various ways.

With respect to terms used in this disclosure, the following definitions are provided.

As used herein, the use of "a," "an," and "the" includes the singular and plural.

In this disclosure, a convention is followed wherein the distal end of the device is the end closest to a patient and the proximal end of the device is the end away from the patient and closest to a practitioner.

As used herein, a "safety needle device" refers to a device having a needle suitable for injection that includes one or more features to prevent needle stick injuries. As used herein, a "passive safety needle" refers to a safety needle device with a passive activation mechanism that automatically covers the distal end of the needle after a patient has been injected.

Reference to "syringe" includes syringes that are indicated for use with needles, nozzle, tubing, or for use in flush systems. As used herein, the term "syringe" refers to a simple pump-like device consisting of a plunger rod that fits tightly in a barrel or tube. The plunger rod can be pulled or pushed along inside the barrel, allowing the syringe to take in and expel a liquid or gas through an opening at the open end of the barrel. The open end of the syringe may be fitted with a needle, nozzle, or tubing to help direct the flow of fluid into and out of the barrel. The syringe may be sterile or unsterile, depending upon the needs of the technician.

Embodiments of the safety needle device of the present disclosure provides a passive activation mechanism that overcomes the deficiencies of the known retracting sheath safety needle devices by allowing for a shorter stroke distance, ease of use, increased patient comfort, low part count, low part complexity, relatively compact design, and clear and unobstructed view of needle in an initial position.

FIGS. 1-6 illustrate an exemplary safety needle device 10 according to the present embodiments of the present disclosure. Safety needle device 10 includes a housing 20 configured to couple to a syringe (not shown). Housing 20 having a proximal end 21, a distal end 22, a housing body 23 and an opening 24 located on the distal end. Tether 30 is disposed on the housing body 23. Tether 30 is generally parallel to a central axis which extends along the housing body 23.

Housing 20 may be of a unitary construction or may be formed from a plurality of components. In one or more embodiments, a proximal end 21 and a distal end 22 of the housing 20 can be separate components that are joined using techniques, such as but not limited to sonic welding, adhesive, snap or press fitting, or the like.

Needle hub 40 is disposed on the proximal end 21 of the housing 20. Needle cannula 42 is attached to the needle hub 40. In one or more embodiments, the proximal end 21 of the housing 20 may be connectable to a luer connection or other fluid connector. As shown in FIG. 1, distal end 22 of housing 20 couples to a retractable sheath 50 such that the retractable sheath 50 is configured to move along a central axis in housing body 23. A channel and an aperture are included in the retractable sheath 50 in order to permit the needle cannula 42 and distal tip 44 of needle cannula 42 to pass therethrough.

Retractable sheath 50 is slidably mounted and movable in the opening 24 of the housing body to slidably accommodate and encase needle cannula 42 projecting axially from housing 20. The proximal end of retractable sheath 50 includes a stop or retention shelf 52 configured to allow the retractable sheath to move between an initial position, a retracted position and an extended position with respect to the housing 20, wherein the initial position partially exposes a distal tip 44 of the needle cannula 42, the retracted position fully exposes the needle cannula 42, and the extended position fully covers the distal tip 44 of the needle cannula 42. In one or more embodiments, the retention shelf 52 may be in the shape of a hook. The term "retractable sheath" is intended to include any sort of tubular member and U-shaped member. The retractable sheath 50 is dimensioned to be compatible with the size and type of needle cannula 40 as will be appreciated by those skilled in the art. The housing 20 includes a housing body 23 with an internal hollow region in which the retractable sheath 50 may move in the proximal and distal direction.

FIG. 1 illustrates a safety needle device 10 that may be removably coupled to a standard or specially configured syringe (not shown). Although the illustrated safety needle device 10 is configured to be coupled to and removed from a syringe, the safety needle device 10 may instead be integrally formed with the syringe. The syringe is generally of a known type suitable for the withdrawal and injection and/or aspiration of fluids or other solutions by way of the safety needle device 10.

Figure 2:
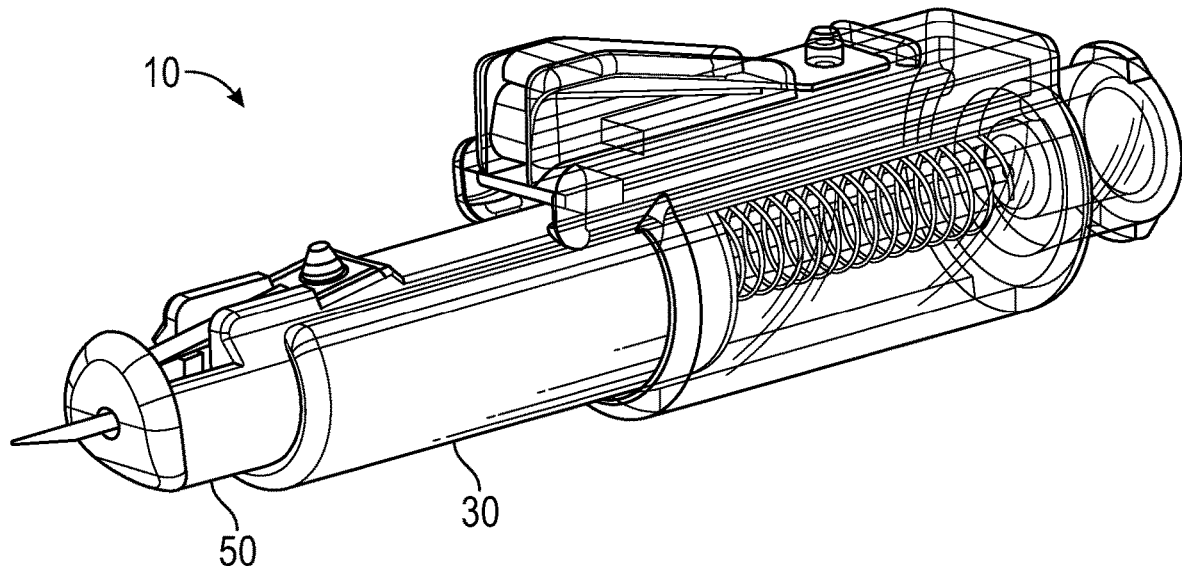
FIG. 2 illustrates a perspective view of a safety needle device shown in FIG. 1 in an initial state.

Referring now to FIG. 1-2, the safety needle device 10 is illustrated in an initial state wherein the retractable sheath 50 is in a partially retracted configuration. Further retraction of the retractable sheath 50 is generally initiated by a practitioner applying pressure on the safety needle device 10 and/or syringe in the distal direction, which thereby encourages the retractable sheath 50 proximally against the bias of the spring element 80. This retraction of the retractable sheath 50 in turn further exposes the distal tip 44 of the needle cannula 42 and initiates penetration by the needle cannula 42 into the patient's skin.

As shown in FIG. 1, needle cannula 42 may be connected to a needle hub 40 disposed at the proximal end 21 of the housing 20 and having a blunted tip (not shown) or beveled tip (as shown in FIG. 1) at the distal tip 44 of needle cannula 42. The needle cannula 42 is disposed in the needle hub 40 in a manner as would be well understood in the art. The needle hub 40 may be integrally formed with the proximal end 21 of housing 20. Needle hub 40 may be configured to be removable or permanently attached to the syringe, or alternatively, needle hub 40 may be integrally formed with the syringe. For example, needle hub 40 may include internal or external threads or other suitable coupling, latching, or locking features such as tabs, slots, projections, pressure/snap fits, and the like, for removably coupling the safety device to a syringe. In some embodiments, the housing 20 includes a generally cylindrically reduced needle support 41 that extends axially from the needle hub 40 to support the needle cannula 42. Housing 20 and/or needle hub 40 are in fluid communication with the needle cannula 42 to permitting fluid to pass between the syringe and the needle cannula 42.

Figure 3:
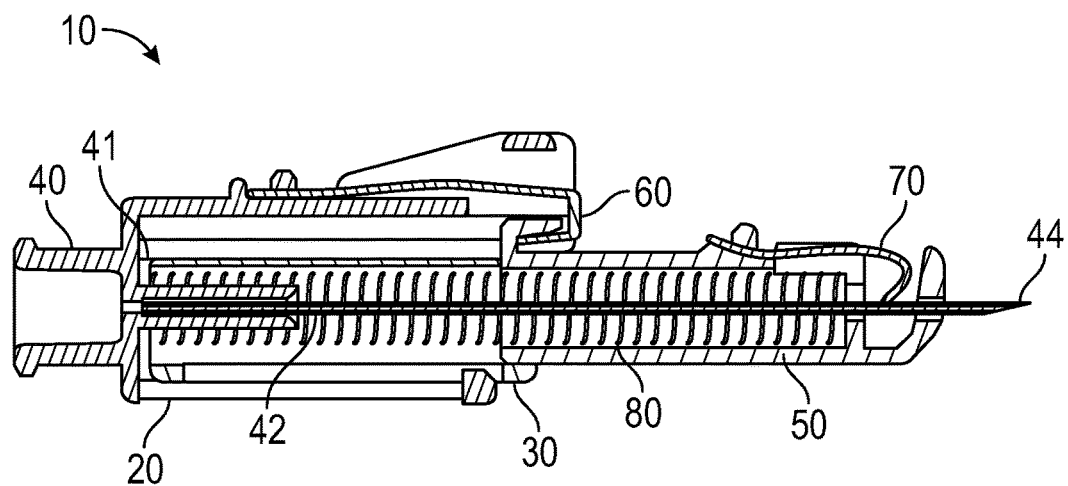
FIG. 3 illustrates a sectional view of a first locking element of the safety needle device shown in FIG. 1.
Figure 4:
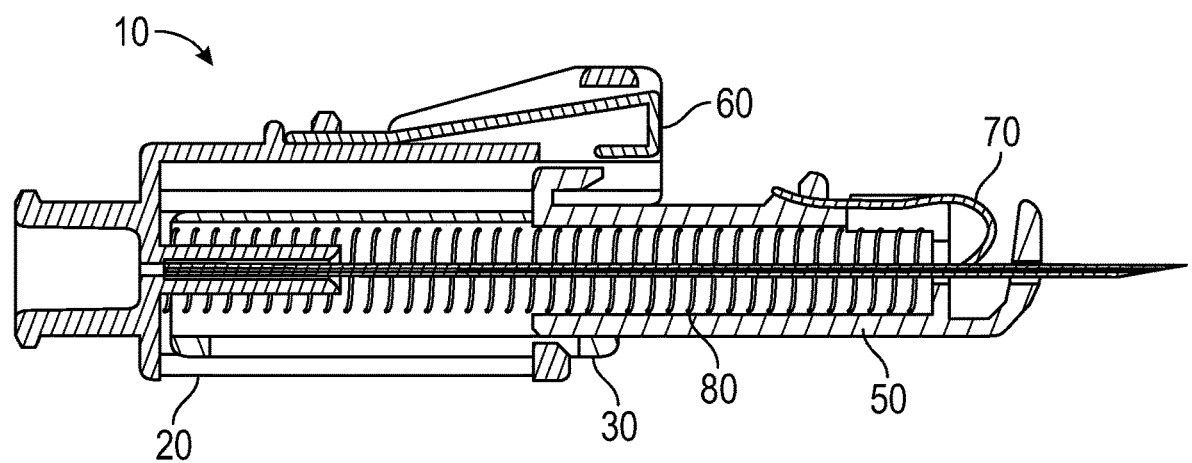
FIG. 4 illustrates another a sectional view of a first locking element of the safety needle device shown in FIG. 1.

The needle cannula 42 extends from the needle hub 40 disposed in the housing 20 and extends to a distal tip 44. In an initial state, as shown in FIGS. 1-3, the distal tip 44 of the needle cannula 42 is partially exposed and protruding from the distal end of the retractable sheath 50 so as to be visible when the retractable sheath 50 is in an initial position, as shown in FIGS. 1-3. The shaft of the needle cannula 42 is increasingly fully exposed from the retractable sheath 50 when the retractable sheath 50 is in a retracted position.

Figure 6:
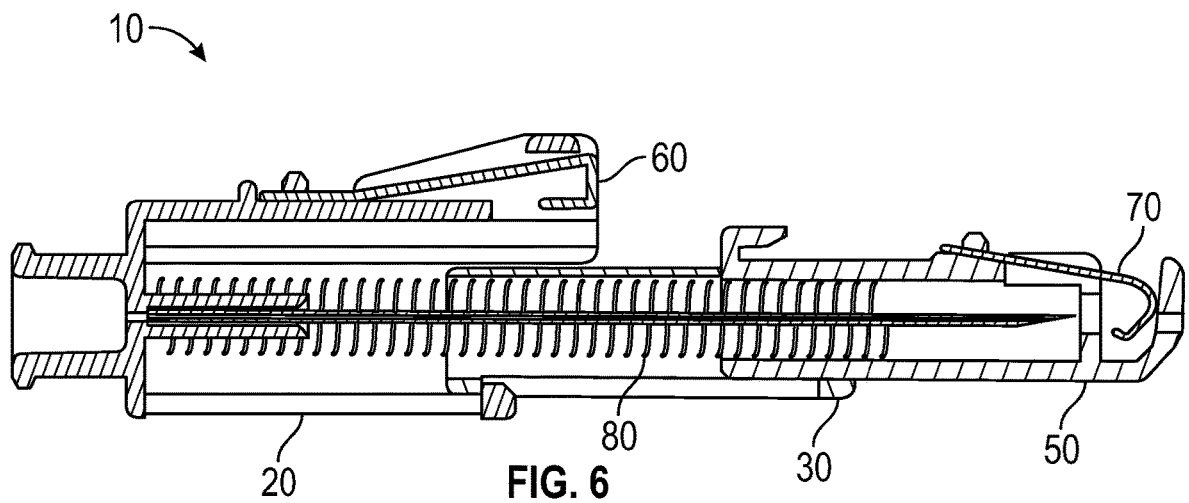
FIG. 6 illustrates another cross-sectional view of a safety needle device according to a first embodiment.
Figure 7:
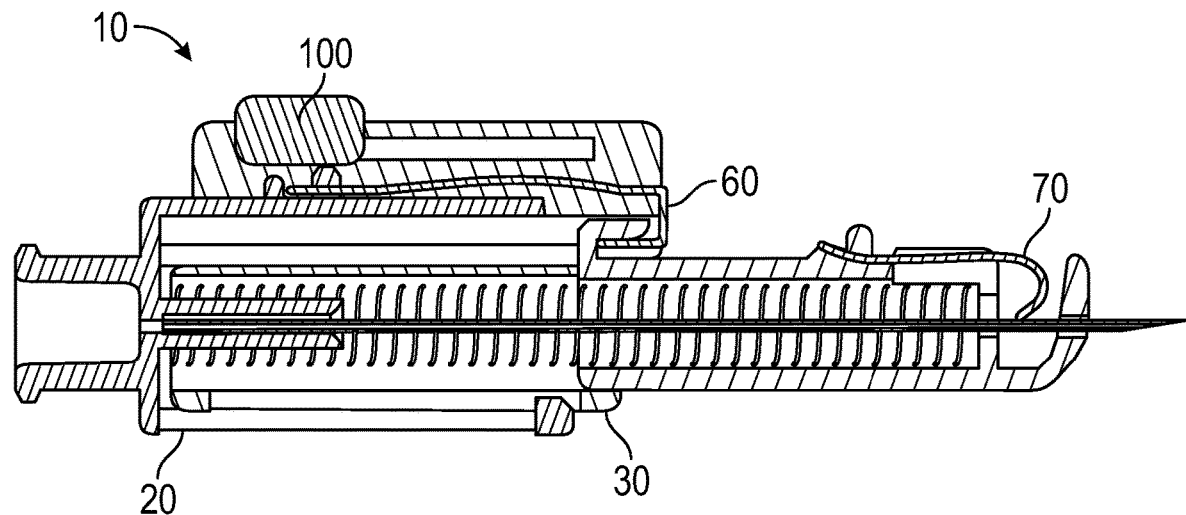
FIG. 7 illustrates a perspective view of a safety needle device shown in FIG. 1 in a retracted state.
Figure 8:
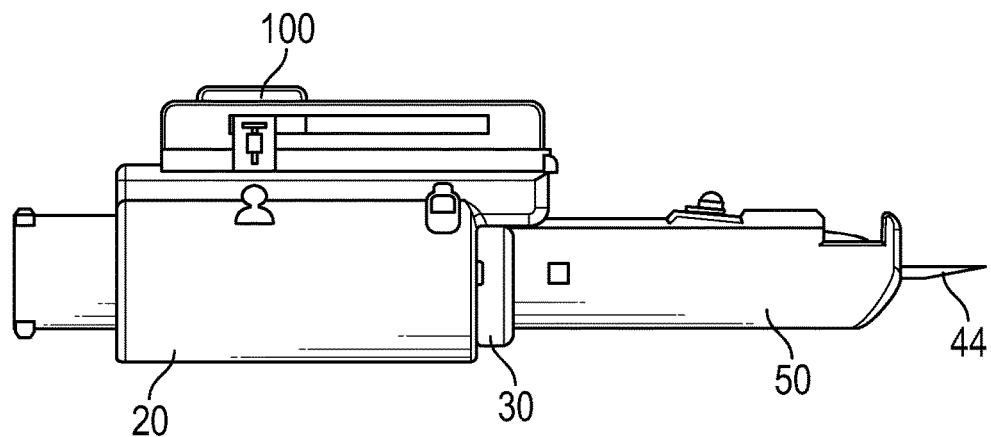
FIG. 8 illustrates a perspective view of a safety needle device shown in FIG. 1 in an extended state.
Figure 9:
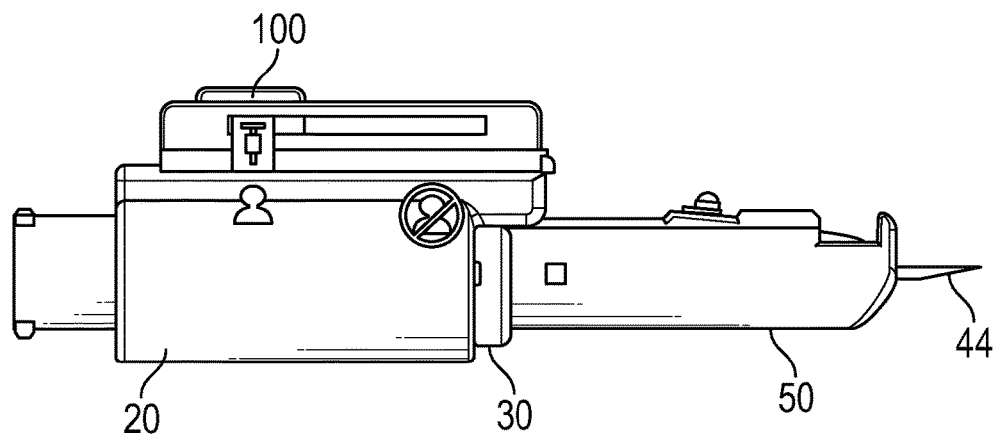
FIG. 9 illustrates a perspective view of a safety needle device according to a first embodiment.

As illustrated in several of the drawings, most notably FIGS. 1 and 2, retractable sheath 50 is generally comprised of a tubular portion and is slidably retractable along the length of the needle cannula 42 such that a distal tip 44 of the needle cannula 42 is partially exposed and protruding from the distal end of the retractable sheath 50 when in an initial position so as to be visible to a practitioner. A substantial or entire portion of needle cannula 42 is exposed when the retractable sheath 50 is in its retracted position. The length of needle cannula 42 which extends from the needle hub 40 in a distal direction is completely encased when retractable sheath 50 is in its extended position, as shown in FIG. 6.

The needle cannula 42 in accordance with the present disclosure can be formed from conventional materials such as steel or more preferably stainless steel. It will be realized by the skilled artisan that medical grade plastics, composites, ceramics, or like materials can be substituted.

The inside diameter of the retracting sheath 50 is selected so that it will fit closely over needle cannula 42. The retracting sheath 50 may be made of any suitable material, but preferably of a polymer which is tough enough to protect needle cannula 42.

The proximal end 51 of retractable sheath 50 includes a retention shelf 52 that extends radially outward from the proximal end of retractable sheath 50 and is configured to engage the activation latch 60 of the housing body 23. As shown in FIGS. 1 and 2, housing 20 has an opening that receives the retractable sheath 50.

In one or more embodiments, retractable sheath 50 may be disposed and movable in the housing body 23. The retractable sheath 50 is spring loaded, and is supplied to the practitioner with the retracting sheath 50 partially covering the needle cannula 42 so that the distal tip of the needle cannula is exposed and visible in an initial state, as shown in FIG. 2. Upon administration of the injection, the retractable sheath 50 moves from an initial position whereby the distal tip 44 of the needle cannula 42 is exposed to a retracted position whereby the needle cannula is increasingly exposed so that the needle cannula may penetrate the injection site.

One aspect of the present disclosure pertains to a safety needle device that allows for either "Inject Only" or "Integrated Fill and Inject" procedures for fluids, including fluids and solutions used in medical procedures. As shown in FIGS. 1 and 2, one or more embodiments of the safety needle device 10 include an activation latch 60 in combination with a spring element 80. As shown in FIGS. 3-6, in the initial state both the activation latch 60 and the spring element 80 hold stored energy. Upon beginning injection, the energy in the activation latch 60 is released once the retention shelf 52 on the proximal end of the retractable sheath 50 is released from engagement with the activation latch 60 upon a practitioner depressing the activation latch over a very short distance.

Once the activation latch 60 is released from the retention shelf 52 on the proximal end of the retractable sheath 50, the practitioner can continue to inject the cannula to their desired depth in a patient or vial by either utilizing the full length of the needle or a significantly shorter distance of the needle cannula. Upon removing the needle cannula 42 from a patient, the retractable sheath 50 automatically advances forward and the stored energy in the spring element 80 is released allowing retractable sheath 50 to continues to be pushed forward until the lockout latch 70 is able to clip over the distal tip 44 of the needle cannula 42 thereby passively locking out the safety needle device 10 and preventing needle stick injury to the practitioner. In one or more embodiments, activation latch 60 may be a metal latch. In one or more embodiments, lockout latch 70 may be a metal latch.

As shown in FIGS. 3-6, in one or more embodiments, safety needle device 10 may operate in an "Inject Only" state, wherein the safety needle device 10 passively locks out after one compression of retractable sheath 50 upon release of the activation latch 60 from retention shelf 52.

During administration of an injection to a patient, the application of force on the needle device by the practitioner in the distal direction and/or depression of the activation latch 60 by the practitioner causes the retractable sheath 50 to move in a proximal direction. In or more embodiments, the retractable sheath translates from the initial position to the retracted position without impediment. A continued application of force by the practitioner in the distal direction causes activation latch 60 to disengage from the retention shelf 52 thus activating the lockout latch 70. In one or more embodiments, the lockout latch 70 includes a metal latch on a distal end of the retractable sheath. Movement of the retractable sheath from the initial position to the retracted position disengages the activation latch 60 from the retention shelf 52. In some embodiments, the activation latch 60 is generally resilient, so that the radially inwardly disposed second ends can flex and then return to the original position even after the ends have been radially outwardly deflected. In one or more embodiments, the activation latch 60 may include a latching member, such as a shelf, clasp, detent, ratchet, or other structure.

Upon completion of an injection to the patient, the practitioner withdraws the needle cannula from the patient, thus causing the stored energy of spring element 80 to allow the retractable sheath 50 to proceed to fully covers needle cannula 42 in the extended position. The spring element 80 biases the retractable sheath 50 in a distal direction to cover the distal tip 44 of needle cannula 42 causing activation of the lockout latch 70 to prevent further translational movement of the retractable sheath 50 within the housing body 23. Movement of the retractable sheath from the retracted position to the extended position engages the lockout latch 70 to a distal tip of the needle cannula.

In one or more embodiments, the lockout latch 70 is disposed on the retractable sheath and rides along the needle cannula until the lockout latch 70 covers the distal tip 44 of the needle cannula 42 in the extended position. In one or more embodiments, the retractable sheath 50 extends in length beyond the lockout latch 70, as seen in FIG. 1. In one or more embodiments, lockout latch 70 comprises a protective clip which can cover the distal tip 44 of the needle cannula 42 in the extended position. In one or more embodiments, the lockout latch 70 inhibits reuse of the safety needle device 10 by inhibiting further translational movement of the retractable sheath 50 within the housing body 23 by covering the distal tip 44 of the needle cannula 42 in the extended position. Needle cannula 42 is obscured from view when the retractable sheath is in the extended position. As shown in FIG. 6, as the injection is completed and the distal tip 44 of needle cannula 42 is pulled from injection site, the stored force of spring element 80 causes the retracting sheath 50 to extend, and at the end of the stroke, a lockout latch extends over the distal tip of the needle cannula 42 to lock the retractable sheath 50 thereby completing a passive safety lock-out. In one embodiment, the lockout latch is a metal clip.

Spring element 80 includes a proximal end, a main body, and a distal end. In one or more embodiments, as shown in FIG. 1, spring element 80 comprises a compression or coil spring. The spring element 80 biases the retractable sheath toward the extended position.

In one or more embodiment, spring element 80 engages and extends between the proximal end of the retractable sheath and the proximal end of the housing. The spring biases the retractable sheath 50 toward an initial position in which the retention shelf 52 of the retractable sheath 50 is biased into engagement with the activation latch located at the distal end of the housing body 23 thereby allowing the distal tip 44 of the needle cannula 42 to be exposed and visible in the initial position. The retractable sheath 50 completely covers the distal tip 44 of the needle cannula 42 in the extended position. Many types of springs may be employed, such as but not limited to a helical coil spring, conical spring, wave-spring, or the like. In some embodiments, the spring element 80 is configured to facilitate retraction of the retractable sheath 50 by a practitioner applying distal pressure to the syringe and/or the safety needle device 10 with just one hand.

Safety needle device 10, and components thereof, can be formed using many manufacturing processes sufficient to provide the desired shape of the components. In some embodiments one or more components are made by a molding process, such as but not limited to injection molding, compression molding, blow molding, transfer molding, or similar. In some embodiments, one or more components are formed by forging, machining, casting, stamping, extrusion, a combination thereof, or the like.

In many embodiments, the safety needle device 10 is constructed from a biocompatible material. In some arrangements one or more of the components of the safety needle device 10 are plastic (e.g. polyurethane, etc.) or metal (e.g., stainless steel, etc.). In some embodiments, the housing 20 and/or the retractable sheath 50 are constructed of materials that are either translucent or opaque.

In some embodiments, movement of the retractable sheath 50 to disengage the retention shelf of the retractable sheath from activation latch 60 will allow for automatically engagement of lockout latch 70 with the distal tip 44 of needle cannula 42. In some embodiments, movement of the retractable sheath 50 from an about fully retracted position to an about fully extended position automatically prevents or inhibits reuse of the safety needle device 10.

In embodiments in which housing 20 comprises multiple pieces, the manufacturing process can include the step of assembling the housing 20. A retractable sheath is formed having retention shelf 52 which is aligned for engagement with activation latch 60. The retractable sheath 50 is slidingly moved through the opening 24. The needle cannula 42 is coupled with the needle support 41 of the housing 20. The spring element 80 is inserted into the housing body 23 and positioned to bias the retractable sheath 50.

Figure 5:
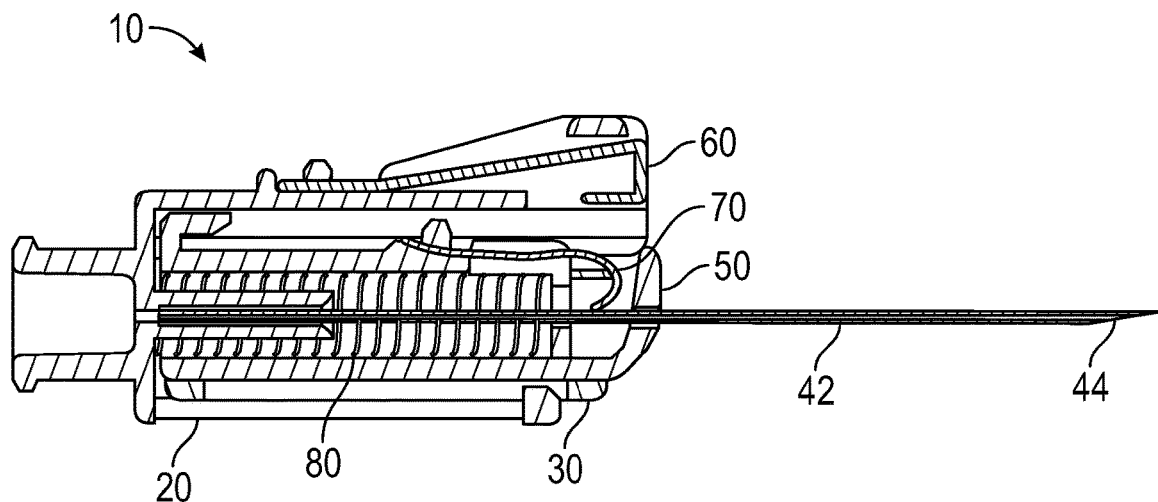
FIG. 5 illustrates a cross-sectional view of a safety needle device according to a first embodiment.

As shown in FIG. 5, as the retractable sheath 50 continues to retract into the housing body 23, to further expose the needle cannula 42. Upon withdrawal of the needle cannula 42 from the patient, the stored spring energy of the spring element 80 to distally extend the retractable sheath 50. As the retractable sheath 50 distally extends, it covers the needle cannula 42 into the channel of the hub body thereby covering the distal end of the needle cannula 42. As shown in FIG. 6, upon reaching the retractable sheath 50 reaching the distal tip 44 of the needle cannula 42, the lockout latch 70 moves distally over the distal tip to cover the distal tip 44 of the needle cannula 42 to prevent reuse of the safety needle device 10. The retractable sheath 50 has been fully extended and fully covers the needle cannula 42. The lockout latch 70 thus presents a physical stop to inhibit the retractable sheath 50 from being proximally retracted again.

Another aspect of the present disclosure pertains to a safety needle device having a telescoping tether having a first end secured to the hub or housing and a second end secured to the retractable sheath. In one more embodiments, incorporation of a telescoping tether allows the overall size of the safety needle device to be significantly reduced. FIGS. 1-12 and 19 show a perspective view of another embodiment having a tether 30.

As shown in FIGS. 1-12 and 19, safety needle device 10 further comprises a tether 30, which connects the housing 20 and is telescoping. As the retractable sheath 50 moves distally along the needle cannula 42, the tether 30 extends to the length of the needle cannula 42. The tether 30 thus provides an extensible length beyond which the housing 20 may not distally extend.

The tether 30, having a proximal end and a distal end, may have the proximal end affixed to housing 20 or hub 40 and the distal end of the tether may be affixed to the retractable sheath 50 by any suitable fastening mechanism including, but not limited to adhesives, point welding, rivets, and heat sealing. In one or more embodiments, tether 30 may be in the form of a tube or concentric cone-shaped enclosures. The tether 30 deploys in the form of a tube or cone-shaped enclosure around the needle cannula 42. Tether 30 extends to form an enclosure around the cannula as retractable sheath is moved distally along the length of the cannula.

Figure 19:
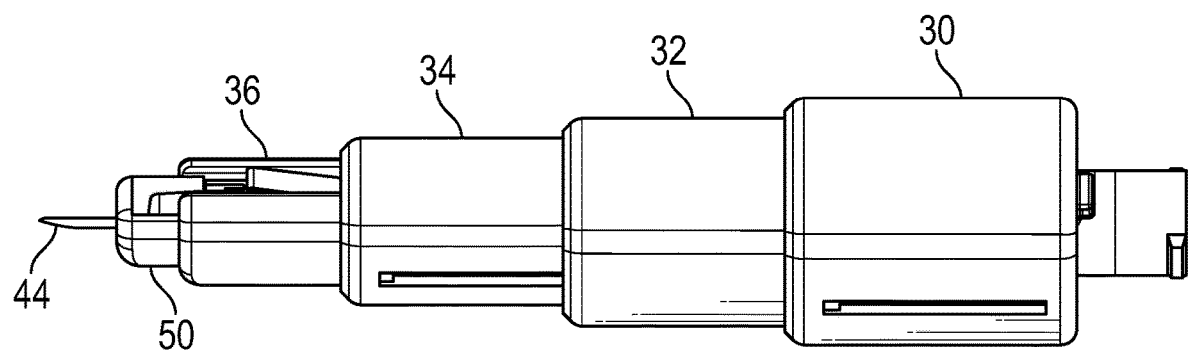
FIG. 19 illustrates a perspective view of a safety needle device according to a first embodiment.

Other configurations for the tether 30 are possible. In one or more embodiments, as shown in FIG. 19, tether 30 may comprise a plurality of substantially concentric shells. In one or more embodiments, tether 30 distally extends along the needle cannula 42, and the concentric shells (32, 34, and 36) of the tether 30 slide past each other to cover or completely envelope the needle cannula 42. In one or more embodiments, the tether extends to form a substantially cone-shaped enclosure around the cannula as the retractable sheath is moved distally along the length of the cannula. In certain embodiments, the tether is a plurality of substantially concentric shells which are axially telescoping and envelope the cannula as the retractable sheath is moved distally along the length of the cannula.

As shown in FIG. 19, tether 30 may include a plurality of concentric shells 32, 34, 36. The outermost concentric shell 32 may be affixed to the inner surface of the housing 20 or needle hub 40, and the innermost concentric shell 36 may be affixed to the retractable sheath 50. Concentric shells 32, 34, 36 are designed to telescopically slide with respect to each other, but not to extend past each other, and the total extension length of the tether 30 is long enough to permit the retractable sheath 50 to cover the length of needle cannula and for lockout latch 70 to extend over and cover the distal tip 44 of the needle cannula. Tether 30 is configured to fully cover needle cannula 42 when the retractable sheath is maximally extended to cover and shield the distal tip 44 of the needle cannula.

Another aspect of the present disclosure pertains to housing 20 further includes a slider element 100 that extends over activation latch 60 extending radially from an external surface of housing 20.

As shown in FIGS. 7-12, safety needle device 10 is configured to enable "fill and inject" wherein activation latch 60 is held down when the safety needle device 10 is in the fill state so that retention shelf 52 on the proximal end of the retractable sheath 50 remains engaged to the activation latch 60 after each fill. As shown in FIGS. 7-12, in one or more embodiments, safety needle device 10 may include a slider element 100 to hold down activation latch 60 to ensure that retention shelf 52 on the proximal end of the retractable sheath 50 remains engaged to the activation latch 60, thus preventing the stored energy in the activation latch 60 from being released. In yet another embodiment, slider element 100 may be configured to toggle in a perpendicular direction with respect to the needle cannula.

Desirably, activation latch 60 is integrally formed with housing 20 extending from an outer surface of hub body. Slider element 100 may also include a contact surface having a profile for accommodating a practitioner's finger. As shown in FIGS. 7-12, slider element 100 is positioned in a longitudinal slot 110, with finger surface extending beyond longitudinal slot 64 at the outer surface of housing 20.

Figure 10:
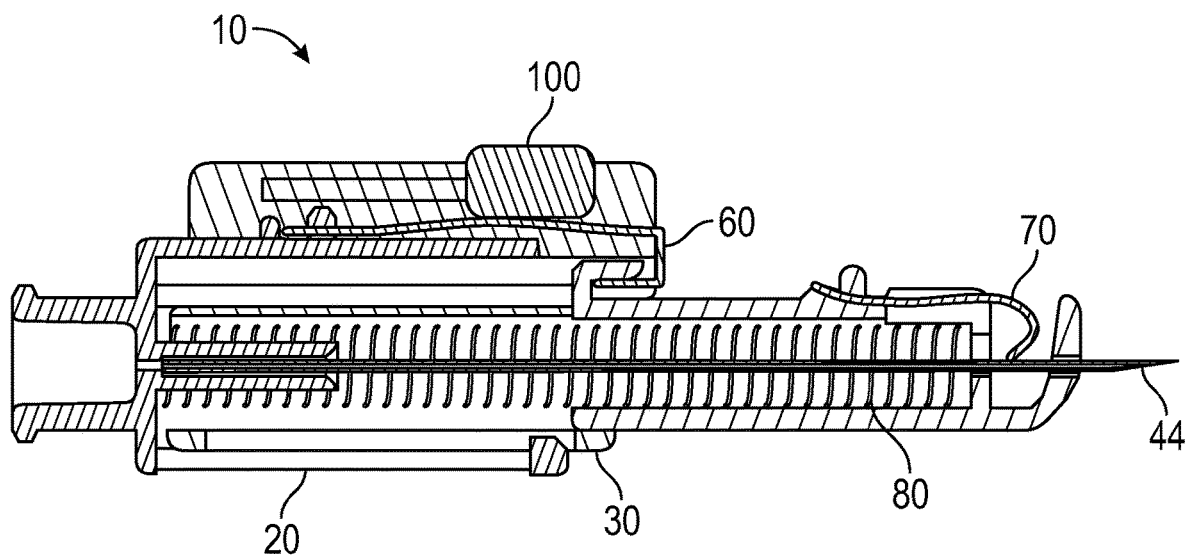
FIG. 10 illustrates a perspective view of a safety needle device according to a first embodiment.
Figure 11:
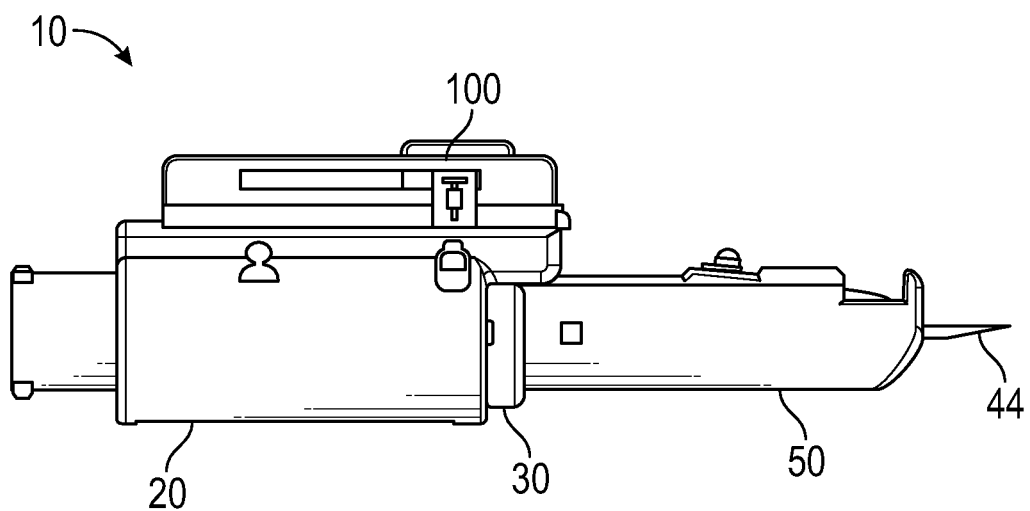
FIG. 11 illustrates a perspective view of a safety needle device according to a first embodiment.
Figure 12:
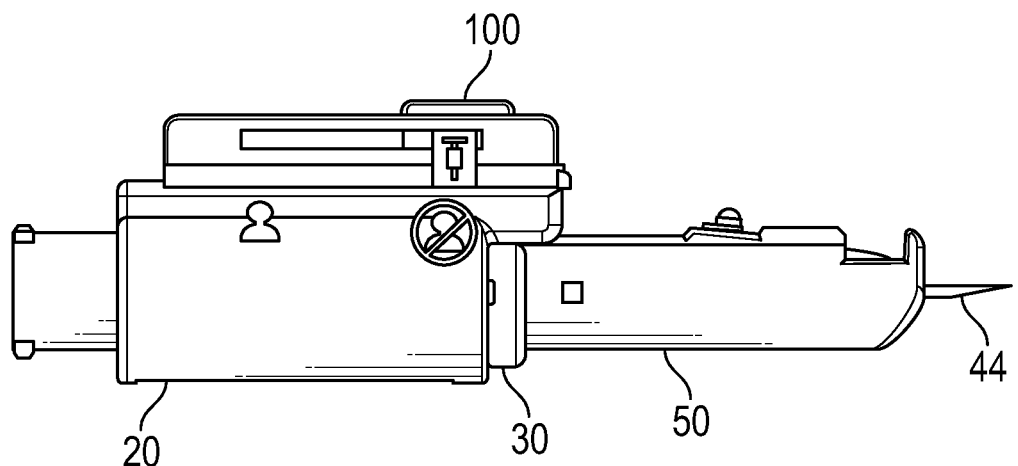
FIG. 12 illustrates a perspective view of a safety needle device according to a first embodiment.
Figure 13A:
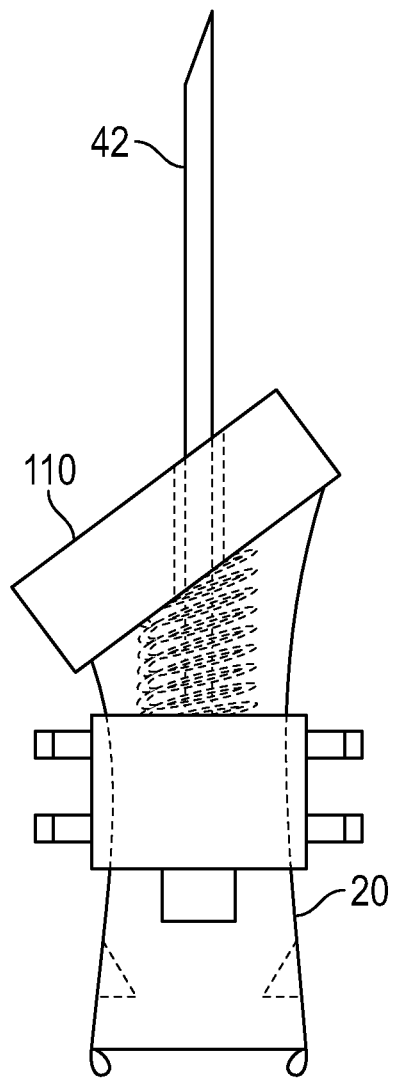
FIGS. 13A and 13B illustrate a perspective view of a safety needle device according to a first embodiment.
Figure 13B:
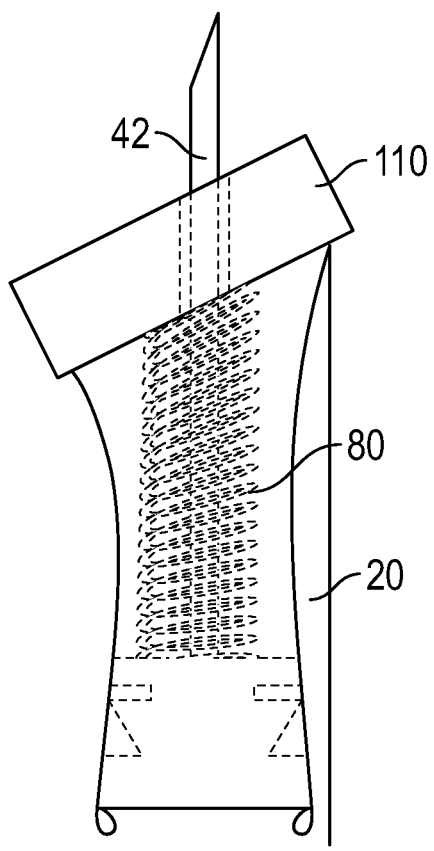

Safety needle device 10 is capable of assuming a position for protection and a position for use by way of translating the slider element 100 from an initial protective position in which the slider element 100 is at the forward slot end of longitudinal slot and extends over the distal end of the activation latch to moving the slider element in an proximal direction such that the slider element extends over the proximal end of the activation latch thus allowing the activation latch from releasing from the slot of the retractable sheath. To prevent retractable sheath 50 from being released from the initial position, slider element 100 is at the forward slot end thus preventing activation latch 60 from releasing from retention shelf 52 of retractable sheath 50. Activation latch 60 locks retractable sheath 50 through engagement with retention shelf 52 disposed on the proximal end of retractable sheath 50 when slider element 100 is located at the forward slot end of longitudinal slot, as shown in FIG. 10.

Once the use moves the slider element 100 at the rearward slot end thus allowing the release of activation latch 60 from the retractable sheath 50 once the retractable sheath is moved in a proximal direction during the administration of an injection to a patient. Upon activation, activation latch 60 releases retractable sheath 50 when activation latch 60 is no longer in an interference engagement with the retention shelf 52 disposed on the proximal end of retractable sheath 50.

Movement of the activation latch from a forward slot end to the rearward slot end disengages the enlarged portion of the protective clip from interference engagement with retention shelf 52 of the retractable sheath. This releases retractable sheath from the locked position, thus allowing free movement of retractable sheath 50 within the housing toward the distal tip 44 of needle cannula 42. In one or more embodiments, this may be accomplished by exerting pressure on finger contact surface of the activation latch 60.

Distal tip 44 of needle cannula 42 is completely covered by the protective clip of the retractable sheath to prevent re-exposure thereof without any further action on the part of the practitioner.

Safety needle device 10 may include means for storing energy extending between housing 20 and retractable sheath 50, such that upon release of the activation latch, retractable sheath 50 is automatically forced forward along longitudinal axis thereby automatically enabling shielding of needle cannula 42.

The means for storing energy may be a spring element 80, such as a compression spring. Spring element 80 may extend between the distal end of retractable sheath 50 and proximal end of housing 20.

The needle safety device of the present disclosure provides a simple mechanism for causing actuation of the shielding feature with a single hand of the practitioner.

In yet another embodiment, as shown in FIGS. 13A-18, a blocking member 120 may utilized in combination with a spring element to pivot that blocking member 120 in order to achieve lockout and thereby preventing the needle from re-finding the hole. In one or more embodiment, blocking member 120 as housed inside the sheath as shown in FIGS. 13A, 13B, 14A and 14B. In one or more embodiment, blocking member 120 may be configured as an integrated block that utilizes a living hinge as shown in FIGS. 15A and 15B. As shown in FIGS. 13A, 13B, 14A and 14B, a sheath may be used that that utilizes the energy in a spring element to bias the sheath upon lockout so that the needle and the hole are no longer co-axial preventing it from once again finding the hole. In one or more embodiments, blocking member 120 may be configured as an angled plastic component.

In one or more embodiments, as shown in FIGS. 13A-15B, blocking element comprises a block having a diagonal channel within the body of the blocking element attached to spring element is provided. In an initial state, the cannula is threaded through the diagonal channel such allowing the distal tip of the cannula to protrude from the distal end of the retractable sheath 50 such that distal tip of the cannula is visible to the practitioner while the spring element exerts force on blocking element to maintain the blocking element in a biased state at the distal end of the retractable sheath 50. Upon administration of an injection to a patient, the retractable sheath 50 moves in a proximal direction such that the needle cannula moves out of the diagonal channel allowing the blocking member to rotate to an unbiased state such that the cannula is prevented the distal tip 44 of needle cannula 42 from re-entering the diagonal channel within the body of the blocking element to prevent exposure of the practitioner from the distal tip 44 of needle cannula 42. It will be appreciated that the blocking element may be mounted to a spring element, or it may be an integral part of, the distal end of the retractable sheath 50.

If the distal tip of the cannula attempts to pass back through the diagonal channel, the distal tip will be buttressed by the body of the blocking member thus causing the distal tip to remain safely disposed within the housing 20 and prevented by the tether 30 and blocking member from exiting the confines of the housing 20.

Figure 14A:
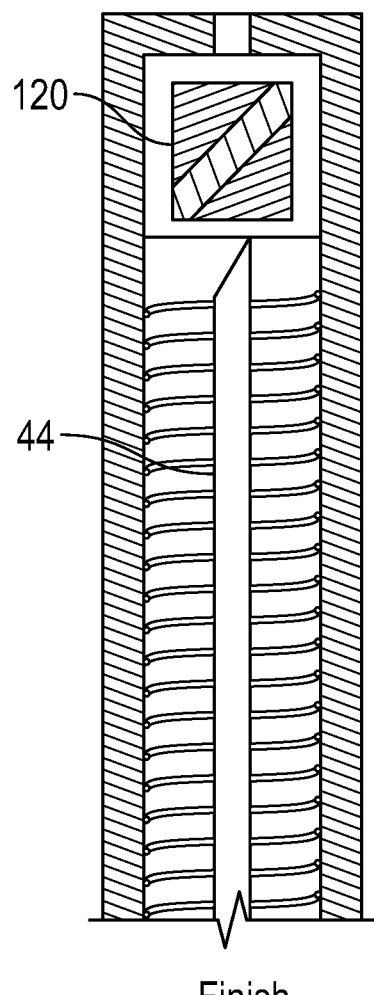
FIGS. 14A and 14B illustrate a perspective view of a safety needle device according to a first embodiment.
Figure 14B:
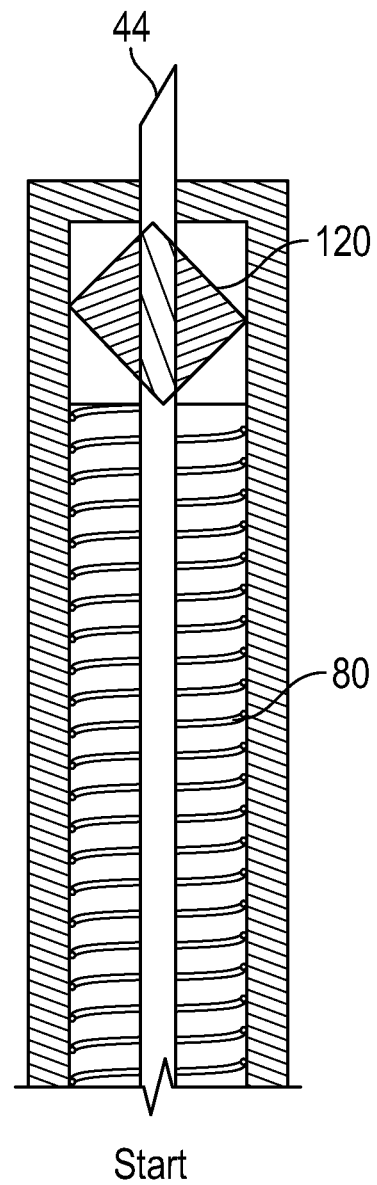
Figure 15A:
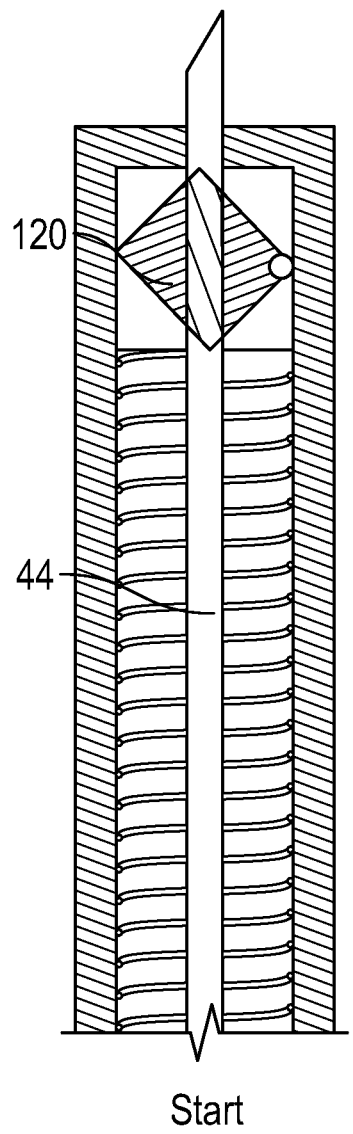
FIGS. 15A and 15B illustrate a perspective view of a safety needle device according to a first embodiment.
Figure 15B:
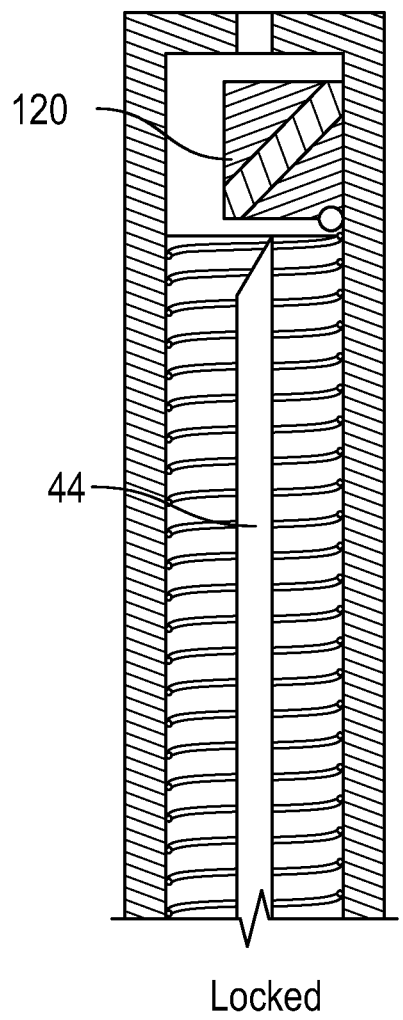
Figure 16:
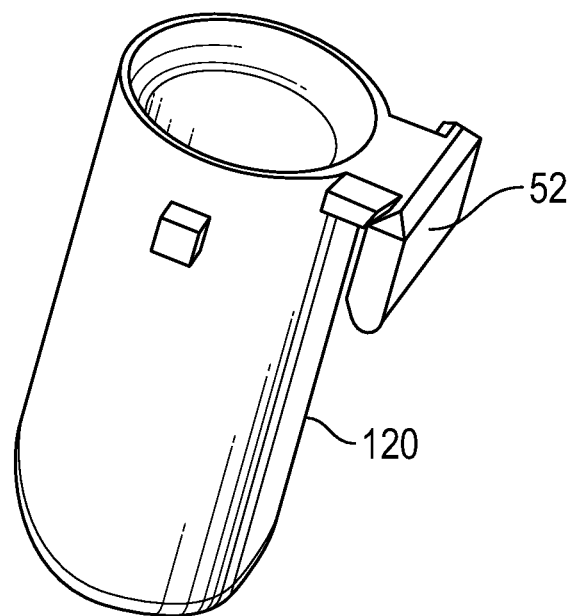
FIG. 16 illustrates a perspective view of a safety needle device according to a first embodiment.
Figure 17:
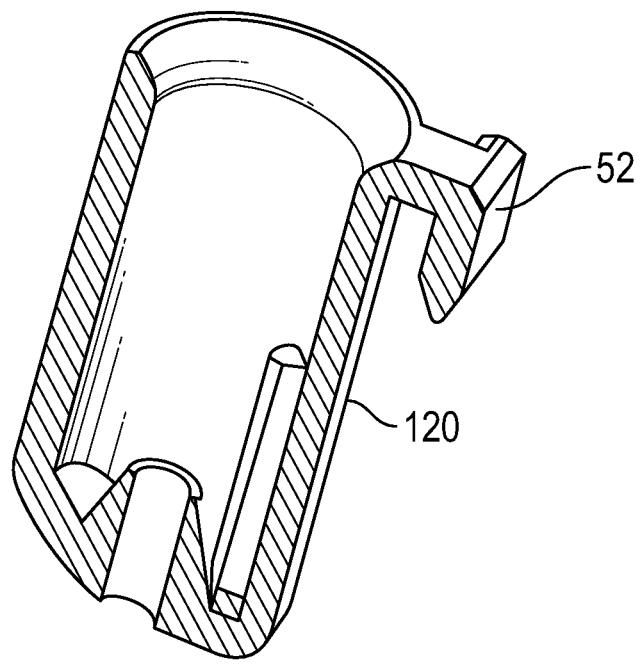
FIG. 17 illustrates a perspective view of a safety needle device according to a first embodiment.
Figure 18:
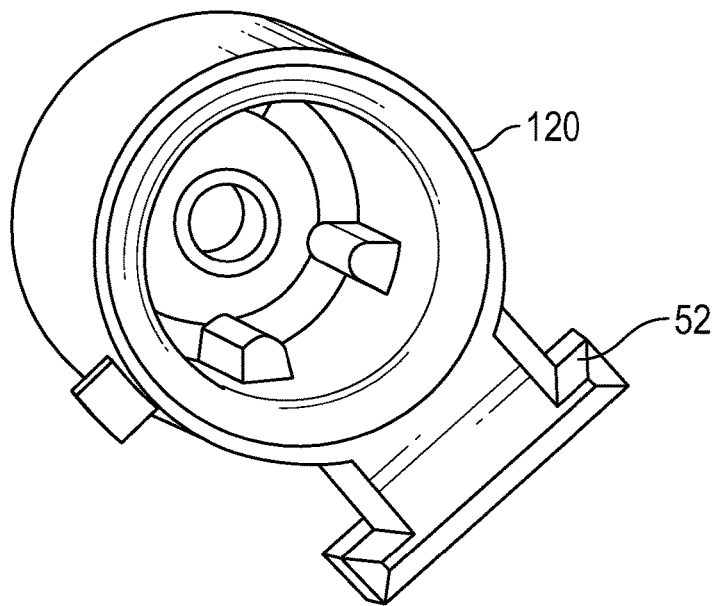
FIG. 18 illustrates a perspective view of a safety needle device according to a first embodiment.

When the needle cannula 42 is withdrawn from the patient, the patient's skin no longer obstructs forward movement of the retractable sheath 50, and the retractable sheath 50 then moves to the extended position as shown in FIG. 14A. As shown in FIGS. 13A-15B, the retractable sheath 50 has an opening through which the needle cannula 42 extends in an initial position.

The misalignment of the needle cannula 42 with the diagonal channel prevents the needle cannula 42 from extending back out of the diagonal channel after use. Furthermore, the blocking element may be made of strong material to prevent the distal tip 44 of the needle cannula 42 from piercing through the blocking element.

In one or more embodiments, the safety needle device 10 can include a cap that is removably coupled to the housing 20 to reduce or prevent contamination of the needle cannula during shipping and storage of the safety needle device 10. The cap is generally kept in the closed position until just prior to an injection and/or aspiration procedure, at which time the cap is removed from the housing 20.

It is also envisioned that in one or more embodiments of the present disclosure, safety needle device 10 does not included includes a tether 30. In such an embodiment, housing 20 has a proximal end 21, a distal end 22, a housing body 23 and an opening 24 located on the distal end. Distal end 22 of housing 20 couples to a retractable sheath 50 such that the retractable sheath 50 is configured to move along a central axis in housing body 23.

Any suitable caps or packaging comprising a safety feature may be used in conjunction with the safety needle device disclosed herein. Any suitable caps or packaging comprising a safety feature may be used in conjunction with the safety needle device disclosed herein. Types of safety features vary in structure and mechanics but exemplary caps or packaging include, but are not limited to, those described in commonly owned, U.S. Patent Application Ser. Nos., 62/433,044, 62/433,526 and 62,433,297, the disclosures of which are incorporated herein by reference in their entireties.

Figure 20:
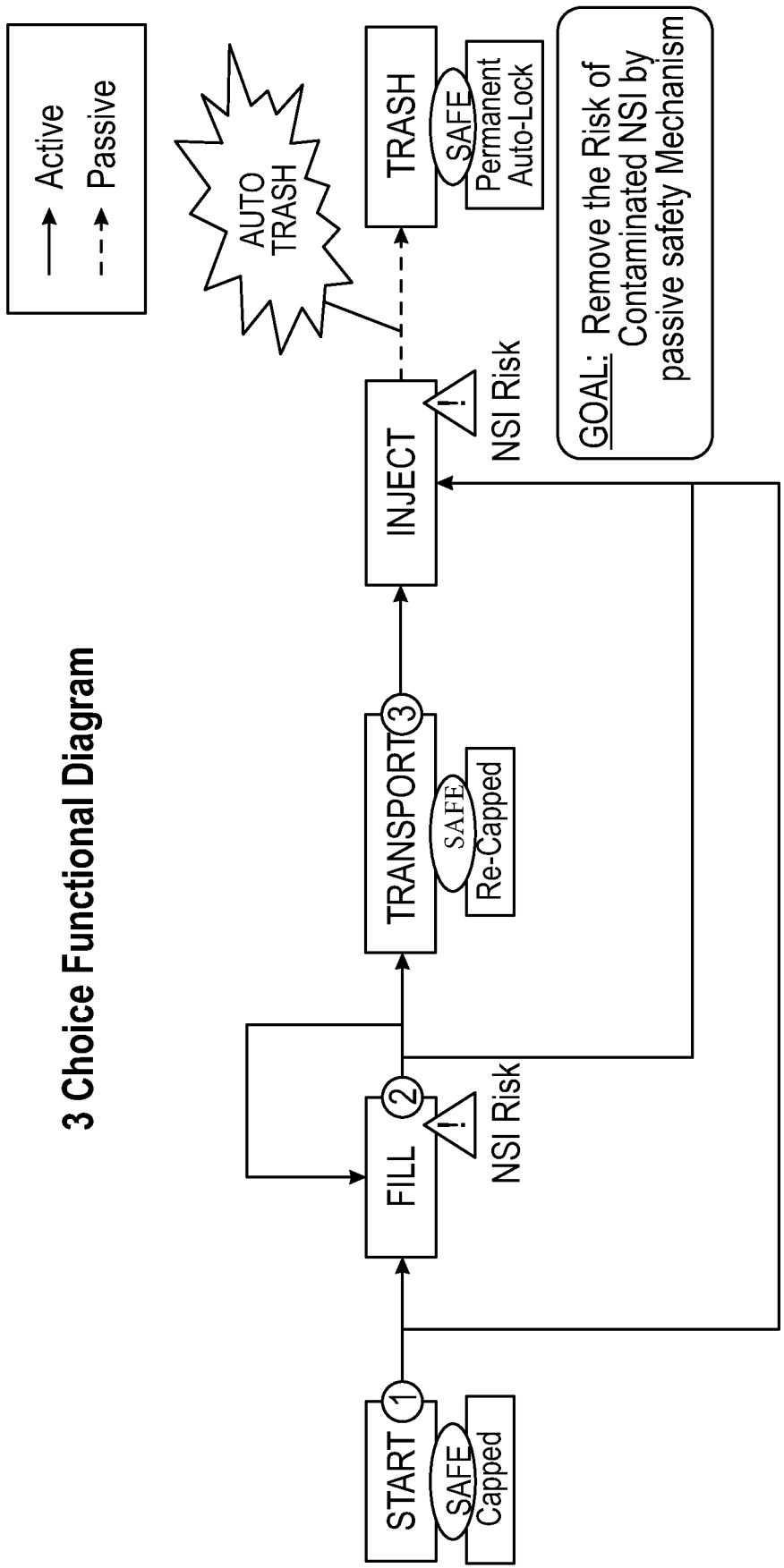
FIG. 20 illustrates a flow diagram for 3 Choice Passive Safety Device Functional Architecture.
Figure 21:
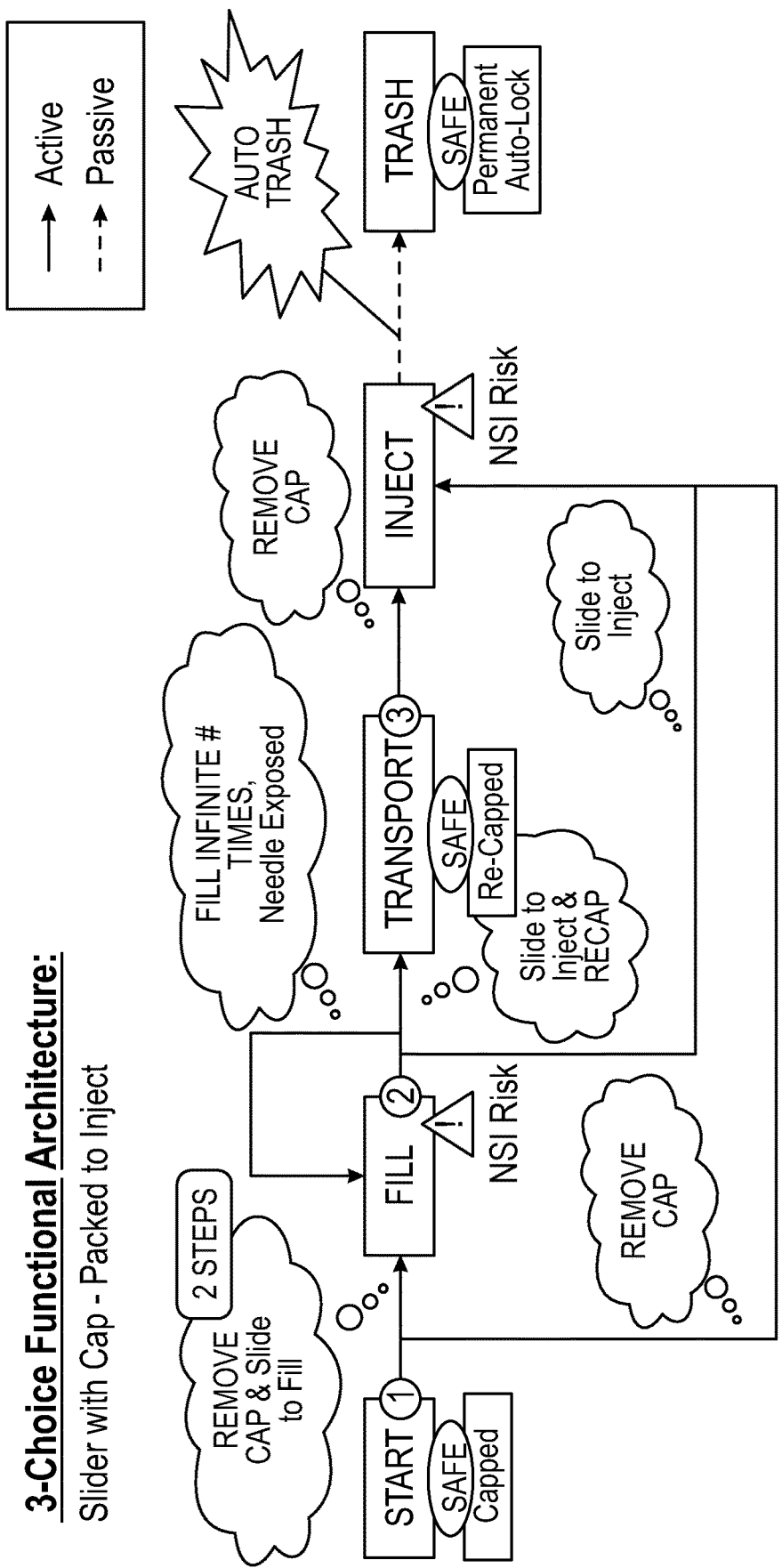
FIG. 21 illustrates a flow diagram for 3 Choice Passive Safety Device Functional Architecture with Slider Cap device.
Figure 22:
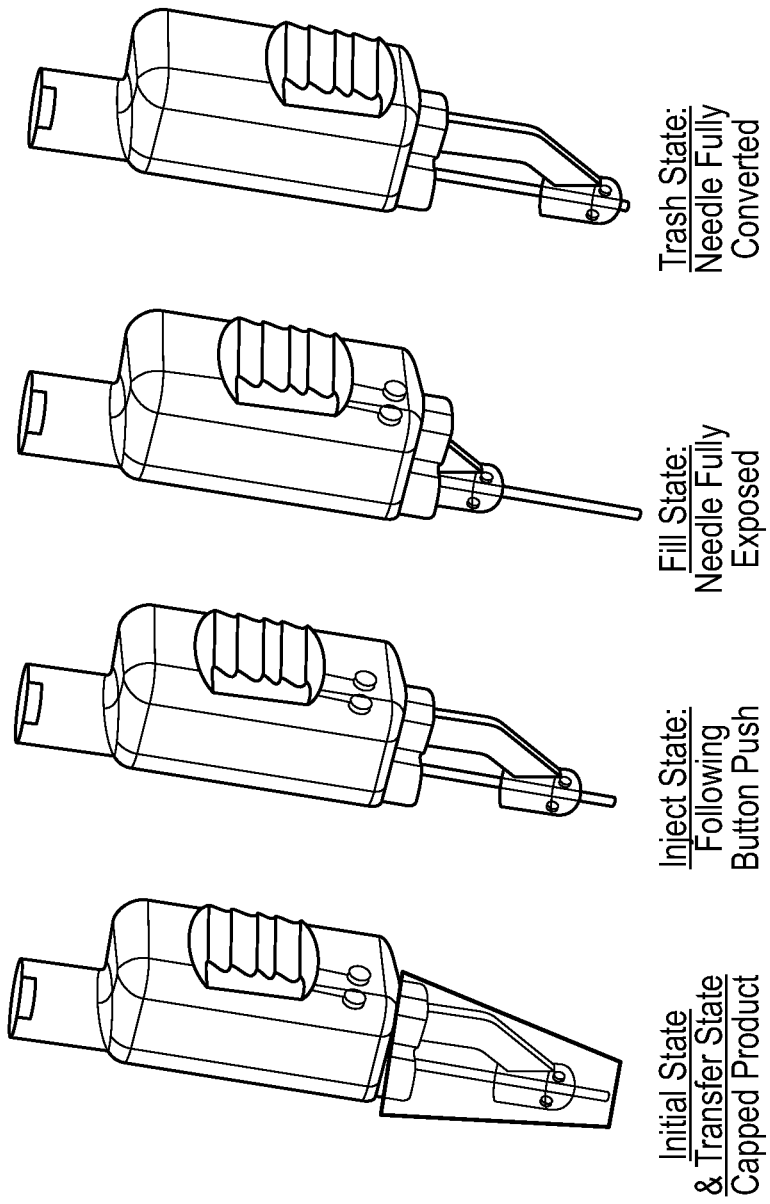
FIG. 22 illustrates a schematic for 3 Choice Passive Safety Device Functional Architecture with Slider Cap device.

Another aspect of the present disclosure pertains to a "3 Choice" Passive Safety Device Functional Architecture which allows a practitioner to both fill and inject with the same needle safety device. During this process the practitioner has the opportunity to make 3 choices throughout the use of needle safety device. FIG. 20 illustrates a flow diagram for 3 Choice Passive Safety Device Functional Architecture. FIG. 21 illustrates a flow diagram for 3 Choice Passive Safety Device Functional Architecture with Slider Cap device. FIG. 22 illustrates a schematic for 3 Choice Passive Safety Device Functional Architecture with Slider Cap device.

As shown in FIG. 20, to start, a safety needle device comes packaged in a safe state in which the needle is covered and prevents needle stick injury (NSI). This can be in the form of a hard-pack or in a blister with a separate cap. At this point the practitioner makes the first choice: whether to a) Fill (e.g. access a vial to fill a syringe or transfer fluids) or b) Inject (insert the needle into a patient to deliver medication). In one or more embodiments, at the first choice, the practitioner may actively change the safety needle device to that state by either activating the activation latch or sliding the slider mechanism to release the activation latch from the retention shelf on the retractable sheath as discussed above. Assuming the practitioner chooses to Fill, once they complete filling, they now make the second choice whether to: a) fill the safety needle device again (e.g. perform another vial access), b) move the product to an inject state, or c) move the product to a transport state. In one or more embodiment, each of these choices requires an active motion by the practitioner. Assuming the practitioner chooses to move the product to the transport state, they now place the safety device needle into a safe state that could prevent NSI's (e.g. place a cap on the safety device needle). Following transportation, the practitioner then needs to make the third choice: whether to actively change the state of product (e.g. move the slider element to allow release of the activation latch from the retention shelf on the retractable sheath) to the inject state. Once in the inject state, within approximately the first 5 mm or less of the needle penetrating the patient's skin (or other medium) the device will automatically lock out by allowing the retractable sheath with its protective clip to cover the distal tip of the needle cannula—thereby defining passive safety. In one or more embodiments, "Fill", "Inject" and "Trash" symbols will be depicted on the safety device needle such that the slider will point to each during that state.

As shown in FIG. 21 and FIG. 22, to start, a safety needle device comes packaged in a safe state in which the needle is covered with a cap, along with a slider element that may be positioned to prevent activation latch from disengaging from the retention shelf of the retractable sheath, as discussed above, to prevent needle stick injury (NSI). At this point the practitioner makes the first choice: whether to a) Fill (e.g. access a vial to fill a syringe or transfer fluids) by removing the cap and sliding the slider element over the activation latch to prevent activation latch from disengaging from the retention shelf of the retractable sheath while filling the device or b) Inject (e.g. removing the cap and insert the needle into a patient to deliver medication). In one or more embodiments, at the first choice, the practitioner may actively change the safety needle device to either a fill state (e.g. by sliding the slider element over the activation latch to prevent release of the activation latch from the retention shelf on the retractable sheath while filling or actively changing the safety needle device) or to an inject state (e.g. by sliding the slider mechanism off of the activation latch to allow for the release of the activation latch from the retention shelf on the retractable sheath during inject state to allow for retractable sheath with its protective clip to cover the distal tip of the needle cannula—thereby defining passive safety. Assuming the practitioner chooses to Fill, once they complete filling, they now make the second choice whether to: a) fill the safety device needle repeatedly over a desired number of times (e.g. perform another vial access), b) move the product to an inject state by sliding the slider mechanism off of the activation latch to allow for the release of the activation latch from the retention shelf on the retractable sheath during inject state to allow for retractable sheath with its protective clip to cover the distal tip of the needle cannula, or c) move the product to a transport state by re-capping the safety needle device with a cap. In one or more embodiment, each of these choices requires an active motion by the practitioner. Assuming the practitioner chooses to move the product to the transport state, they now place the safety device needle into a safe state that could prevent NSI's (e.g. place a cap on the safety device needle). Following transportation, the practitioner then needs to make the third choice: whether to actively change the state of product (e.g. removing the cap and moving the slider element to allow release of the activation latch from the retention shelf on the retractable sheath) to the inject state. Once in the inject state, within approximately the first 5 mm or less of the needle penetrating the patient's skin (or other medium) the device will automatically lock out by allowing the retractable sheath with its protective clip to cover the distal tip of the needle cannula—thereby defining passive safety.

FIG. 22 shows the safety needle device in an initial state and transfer state (with cap positioned on the safety needle device); inject state (distal tip of the needle cannula partially exposed and visible to the practitioner); fill state (needle cannula fully exposed); and trash state (with the distal tip of the needle cannula fully covered by the retractable sheath and protective clip.

In one or more embodiments, symbols for "Fill", "Inject", and "Trash" may be depicted on the safety needle device. In one or more embodiments, slider element 100 will point to the appropriate symbol for "Fill", "Inject", or "Trash" to indicate the status of the safety needle device. In one or more embodiments, safety needle device comes packaged with a cap in an Inject State with only the needle tip exposed. To inject, remove the cap and inject after which the safety needle device permanently locks out. To Fill, practitioner moves the slider element from the "Inject" to "Fill" Symbol and fill an infinite number of times during which no force will be imparted on the vial. To Transfer the safety needle device, the practitioner places the cap back onto the safety needle device.

Whenever the safety needle device is in a "fill state" it is in a state that allows for potential needle stick injury and when the needle enters into a vial (or other medium) and then exits, it does not lock. This means that a practitioner could access a vial to fill an infinite number of times. Similarly, whenever the device is in an "inject state" it is in a state that also allows for potential needle stick injury. However, once the needle enters into a patient (or other medium) then then exits it automatically locks after 1 time.

A practitioner can move the Inject State at any point in the process. This means that the practitioner can go from state to inject, fill to inject, or transport to inject as indicated above.

As shown in FIGS. 20-22, the needle safety device is delivered to the practitioner in a safe state packaging in which the needle is covered and thus prevents needle stick injury (NSI). Packaging can be in the form of a hard-pack or in a blister with a separate cap. At this point the practitioner makes the first choice: to either a) "Fill" by accessing a vial to fill a syringe or transfer fluids, or b) Inject by inserting the needle into a patient to deliver medication—and they actively change the device to that state. Assuming the practitioner chooses to Fill, once they complete filling, they now make a second choice: whether to a) fill again by performing another vial access; b) move the product to an inject state, or c) move the product to a transport state. Both the first choice and the second choice require an active motion by the practitioner. If the practitioner chooses to move the product to the transport state, the practitioner places the needle safety device into a safe state that could prevent needle stick injury (NSI). Following transportation, the practitioner can subsequently make a third choice: whether to actively change the needle safety device to an inject state. Once the needle safety device is in the inject state, within approximately the first 5 mm or less of the needle penetrating the patient's skin (or other medium) the needle safety device will automatically lock out.

While the needle safety device is in a "fill state", safety needle device may allow for potential needle stick injury because as the needle of the needle safety device enters into a vial (or other medium) and then exits, the needle safety device does not lock. This means that a practitioner could access a vial to fill an infinite number of times.

Similarly, whenever the safety needle device is in an "inject state" it is in a state that also allows for potential needle stick injury. However, once the needle enters into a patient (or other medium) then then exits it automatically locks after 1 time.

In one or more embodiments, the practitioner can move the needle safety device into the Inject State at any point in the process. Thus, the practitioner can actively transition from inject to fill, fill to inject, or transport to inject.

In one embodiment, a needle safety device having a slider element along with a cap may be packaged to Inject. However, if the practitioner decides to fill the safety needle device, the practitioner may proceed to fill after removing the cap from the needle safety device. Alternatively, if the practitioner decides to proceed directly to an inject state, the practitioner may proceed to inject after removing the cap from the needle safety device, whereby after the injection is completed the safety needle device would proceed to a permanent lock out state. Similarly to fill prior to injection, the practitioner would need to move the axial slider from the Inject to Fill State, fill as many times as the practitioner desired, and then the practitioner would proceed to move the axial slider back to the inject state prior to injection. In one or more embodiments, the slider would have a pointer and symbols and/or verbiage to help guide the practitioner. If transport of the needle safety device is desired between fill and inject, the practitioner would need to recap the needle.

This passive safety activation will help to reduce the incident of contaminated needle stick injuries by ensuring that the device automatically locks after injection when used as intended. Additionally, the needle safety device allows practitioners to fill and inject within one product allowing for reduced materials, time savings, and a reduction of cost to clinicians. Additionally, embodiments of the present disclosure allow for utilization of a greater distance of the needle to fill allowing it to penetrate more stoppers that are on the currently available, as well as, providing a more "immediate" lock out when injecting a patient.

Reference throughout this specification to "one embodiment," "certain embodiments," "various embodiments," "one or more embodiments" or "an embodiment" means that a particular feature, structure, material, or characteristic described in connection with the embodiment is included in at least one embodiment of the disclosure. Thus, the appearances of the phrases such as "in one or more embodiments," "in certain embodiments," "in various embodiments," "in one embodiment" or "in an embodiment" in various places throughout this specification are not necessarily referring to the same embodiment of the disclosure. Furthermore, the particular features, structures, materials, or characteristics may be combined in any suitable manner in one or more embodiments.

Although the disclosure herein provided a description with reference to particular embodiments, it is to be understood that these embodiments are merely illustrative of the principles and applications of the disclosure. It will be apparent to those skilled in the art that various modifications and variations can be made to the present disclosure without departing from the spirit and scope thereof. Thus, it is intended that the present disclosure include modifications and variations that are within the scope of the appended claims and their equivalents.

What is claimed is:

1. A safety needle device, comprising:
   a housing configured to couple to a syringe, the housing having a proximal end, a distal end, and a housing body;
   a needle hub disposed on the proximal end of the housing;
   a needle cannula attached to the needle hub;
   an activation latch disposed on an outer surface of the housing body;
   a slider element positioned in a longitudinal slot disposed over the activation latch, the longitudinal slot having a forward slot end and a rear slot end;
   a retractable sheath on an inner surface of the housing body, the retractable sheath having a proximal end and a distal end,
   a retention shelf disposed on the proximal end of the retractable sheath;
   a lockout latch disposed on retractable sheath to cover a distal tip of the needle cannula;
   the retention shelf releasably engaged to the activation latch in an initial position, wherein the initial position partially exposes the distal tip of the needle cannula; and
   a spring element disposed in the housing body and attached to the distal end of the retractable sheath.

2. The safety needle device of claim 1, wherein the activation latch is held down by the slider when the safety needle device is in a fill state such that the retention shelf remains engaged to the activation latch after a fill.

3. The safety needle device of claim 1, wherein the activation latch locks retractable sheath through engagement with the retention shelf.

4. The safety needle device of claim 1, wherein the activation latch releases the retractable sheath when the activation latch is no longer in an interference engagement with the retention shelf.

5. The safety needle device of claim 1, wherein the slider element includes a contact surface having a profile for accommodating a practitioner's finger.

6. The safety needle device of claim 1, wherein the slider element is configured to toggle in a perpendicular direction with respect to the needle cannula.

7. The safety needle device of claim 1, the retractable sheath further comprising a protective clip having an enlarged portion.

8. The safety needle device of claim 7, wherein movement of the activation latch from the forward slot end to the rear lot end disengages the enlarged portion of the protective clip from interference engagement with retention shelf of the retractable sheath.

9. The safety needle device of claim 1, wherein the slider element is in the initial protective position in which the slider element is at the forward slot end of longitudinal slot and extends over the distal end of the activation latch.

10. The safety needle device of claim 9, wherein the slider element is in a non-protective position in which the slider element is at the rear end slot and extends over the proximal end of the activation latch allowing the activation latch to release from the retention shelf of the retractable sheath.

\* \* \* \* \*